United States Patent [19]

Johnson et al.

[11] 4,002,459

[45] Jan. 11, 1977

[54] GERMINATION FACTORS

[75] Inventors: Alan W. Johnson; Gerald Rosebery, both of Brighton, England

[73] Assignee: International Development Research Center, Ottawa, Canada

[22] Filed: Apr. 8, 1975

[21] Appl. No.: 566,098

[30] Foreign Application Priority Data

Apr. 18, 1974 United Kingdom ............ 16990/74

[52] U.S. Cl. .............................. 71/88; 260/240 R; 260/343.2 R; 260/343.3 R; 260/343.6; 260/347.3; 260/347.5; 260/586 F

[51] Int. Cl.$^2$ ...................................... C07D 407/12

[58] Field of Search ................ 71/88; 260/343.2 R, 260/343.3, 240 R

[56] References Cited

UNITED STATES PATENTS 3,075,998  1/1963  Lardelli, et al. ................ 260/343.6

OTHER PUBLICATIONS

Iino et al., Chem. Abst. 78: 110496j (1973).
Harmon et al., Chem. Abst. 79: 41847f (1973).
Cassady et al., Chem. Abst. 81: 169374 (1974).

Primary Examiner—Cecilia M. S. Jaisle
Attorney, Agent, or Firm—Larson, Taylor and Hinds

[57] ABSTRACT

Active compounds, some of which are new, are described for the control of various parasitic weeds of the genus Striga and Orobanche. These compounds all include cyclic lactone structures and are related to the naturally occurring substance strigol. Methods of synthesis of the compounds are given, as well as compositions and methods for controlling the parasitic weeds.

18 Claims, No Drawings

GERMINATION FACTORS

BACKGROUND OF THE INVENTION

The present invention relates to the control of certain parasitic weeds and to weed control compositions suitable for this purpose, as well as to certain new chemical compounds possessing the requisite biological activity. More particularly the invention relates to the control of the weeds *Striga hermonthica*, *S. asiatica* (lutea), *Orobanche crenata*, *O. ramosa* and *O. aegyptiaca* which are parasitic on certain economically important crops such as sorghum, maize, sugar cane and/or broad beans.

Striga causes serious losses in sorghum production and its control is highly desirable since sorghum is the principal subsistence cereal grain for more than 300 million people living in arid tropcial countries. One of the reasons it is difficult to control this weed is that its seeds can remain viable in the soil for as long as 20 years, only germinating in close proximity to the host plant. Thus, control of Striga by rotation of crops or leaving the sorghum fields fallow for a year or more is ineffective since the seeds germinte only when the host plant is sown and starts to grow. Control by planting "false hosts", i.e. plants which trigger germintion of the parasite but which do not act as hosts, is usually uneconomical since such planting must replace the desired crop. Another reason Striga is difficult to control is that since it is parasitic in nature, it draws all its nourishment from its host plant, e.g. sorghum, and is not readily amenable to control by normal weed killers, even those which are selective against certain classes of the weeds.

DESCRIPTION OF THE PRIOR ART

It has recently been shown that germination of the Striga seeds is caused by a substance secreted by the roots of the host plant. This substance has been given the name strigol (Cook et al, J. Amer. Chem. Soc. 1972, 94, 6198) and is represented by the structure Neither its synthesis, which hs recently been reported, nor its isolation from the root exudate of the sorghum or other host plant, offers an economic route to control of Striga. However, if a readily available, such a substance could be used to control Striga by application to the soil containing the dormant seed of the parasite at a time when the host plant was not growing, whereupon the Striga seeds would germinate and, having no host plant to parasitize, would die through lack of nutrition. A similar approach to the control of Orobanche would be attractive.

Cassady and Howie, J.C.S. Chem. Comm. 1974, p. 512 have recently reported the synthesis of certain dilactones related to strigol. These authors coupled the sodium enolate salt of 2-hydroxymethylene-γ-butyrolactone with 4-bromobut-2-enolide or with its 5-methyl derivative to yield compounds of the structure

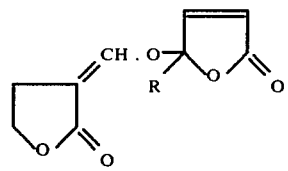

wherein R is hydrogen or methyl.

SUMMARY OF THE INVENTION

The present invention is based on the discovery of certain chemical compounds which are able to act as germination stimulants for the seeds of *Striga hermonthica*, *S. asiatica*, *Orobanche crenata*, *O. ramosa* and *O. aegyptiaca*, and which are comparatively easily synthesized. According to the present invention, there is provided a method for controlling at least one of the above named parasitic weeds by contacting dormant seeds thereof, in the absence of an actively growing host plant, with a compound corresponding to one of the formulae

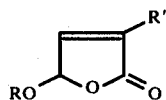

(I)

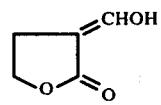

(II)

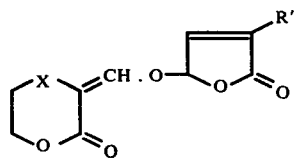

(III)

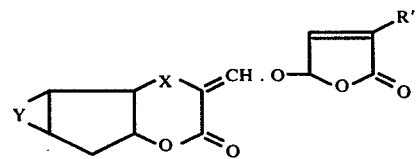

(IV)

wherein R is H or $C_1$ to $C_8$ alkyl, particularly $C_2H_5$ or $CH(CH_3)_2$, R' is H or $C_1$ to $C_5$ alkyl, particularly methyl, X represents a single bond or a —$CH_2$— linkage, and Y represents two hydrogen atoms, an additional bond or an epoxy group.

DETAILED DESCRIPTION OF THE INVENTION

According to one embodiment of the invention, the compounds of formulae (I), (III) and (IV) above are those of the formulae

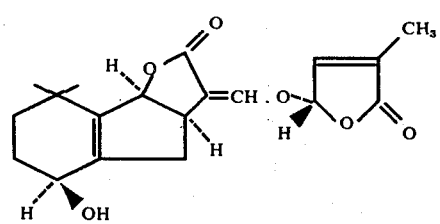

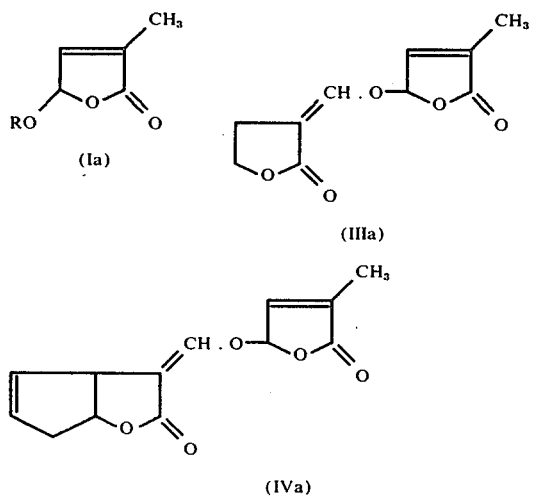

wherein R in formula (Ia) is H or lower alkyl of up to 8 carbon atoms, particularly $C_2H_5$ or $CH(CH_3)_2$.

By the expression "in the absence of an actively growing host plant" is meant either that the host plant is completely absent from the soil containing the parasitic weed seeds being treated, or that the host plant has substantially reached maturity so that any infestation of the host plant by the parasitic weed following germination of the seeds thereof will have a minimal effect on the host plant and harvesting of the latter or natural death at the end of the growing season will prevent the parasitic weed from reaching maturity and consequently re-seeding itself.

The invention also consists in herbicidal compositions comprising an active compound of the structure (I), (II), (III) or (IV), together with a suitable carrier. In addition, the invention consists in the new compounds of these structures, i.e. (I) [R is $C_3$ to $C_8$ alkyl and R' is H or $C_1$ to $C_5$ alkyl] (III) [wherein R' is $C_1$ to $C_5$ alkyl and X is a single bond, or wherein X is a —$CH_2$— linkage and R' is H or $C_1$ to $C_5$ alkyl] and (IV) [wherein R' is $C_1$ to $C_5$ alkyl, X is a single bond and Y is an additional bond or an epoxy group, or wherein R' is $C_1$ to $C_5$ alkyl, X is a —$CH_2$— linkage and Y is two hydrogen atoms, a single bond or an epoxy group].

A preferred aspect of the invention consists in compounds of formula (I) wherein R is $CH(CH_3)_2$ and R' is methyl; formula (III) wherein R' is $CH_3$ and X is a single bond; and formula (IV) wherein R' is methyl, X is a single bond and Y is an additional bond, and methods and compositions utilizing such compounds as well as the compound of formula (I) in which R is $C_2H_5$ and R' is methyl.

The invention also consists in a process for the preparation of the compounds of formulae (III) and (IV) which comprises coupling an alkali metal salt, such as the sodium salt, of a compound of formula (II) with the methylsulphonate derivative of a compound of formula (I) wherein R is hydrogen. This synthesis has unexpected advantages over the subsequently proposed synthesis employing a bromo derivative of a compound of formula (I) wherein R is hydrogen, namely, it proceeds more readily, gives higher yields and is more economical, since the bromo derivatives are unstable and tend to re-arrange.

The active compound of formula (I), (II), (III) or (IV) is preferably applied to the soil containing the dormant parasitic weed seeds in the form of a composition containing the active compound in admixture with a suitable inert carrier or diluent. Suitable carriers or diluents are particularly finely divided solid inert carriers or diluents such as powdered chalk, powdered clays, or powdered conventional fertilizers. Also suitable are liquid carriers. Pre-mixes of a relatively high concentration of the active agent with a carrier may be formulated for ease of handling, particularly for ease of preparing the final composition to be applied to the soil. For instance, such a pre-mix may take the form of a solution of the active compound in an inert organic solvent, such solution also containing a surface active agent selected to promote the formation of an aqueous emulsion when the concentrate is diluted with a large volume of water.

The active compound of formula (I), (II), (III) or (IV) may be applied to the soil containing the parasitic weed seeds in amounts of from 100 to 5000 grams/hectare or from 0.01 to 0.5 grams/cubic meter of soil, and for this purpose compositions may be used containing from 0.001 to 1000 parts per million of the active compound, the balance of such compositions being essentially inert diluent or carrier as described above. The actual concentration of the active compound is of little importance compared with its rate of application to the soil. Too little of the active compound may secure insufficient germination of the parasitic weed seeds to afford effective control. Naturally, temperature and moisture conditions in the soil should be suitable for the germination of the parasitic weed seed.

While compounds of formula (I) wherein R is $C_3$ to $C_8$ alkyl, e.g. $CH(CH_3)_2$ have not previously been reported, they are homologues of the known compound (Ia) wherein R is $C_2H_5$ and may be prepared by the usual esterification procedures from the known compound (Ia) wherein R is H, e.g.

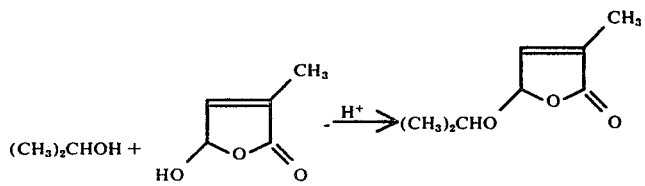

As illustrative of the preparation of compounds (III) and (IV), compound (IIIa) for instance may be prepared by reacting an alkali metal salt, such as the sodium salt, of the known compound (II) with a sulphonate derivative of the lactone (Ia; R=H):

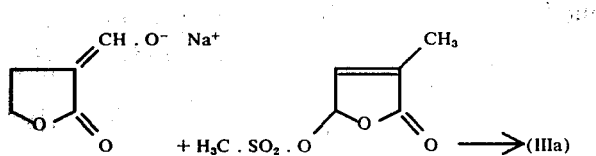

The compound (IVa) may be prepared by an analogous procedure, i.e.

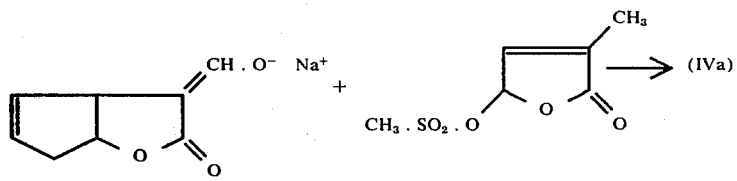

Similarly, the compounds (III) and (IV) in X is a —CH₂— linkage and Y when present is two hydrogen atoms or a single bond, may be prepared analogously from 2-hydroxymethyl-δ-valerolactone sodium enolate salt or its cyclopentano or cyclopenteno derivative, while the compounds (IV) in which Y is epoxy may be prepared by epoxidation of the corresponding unsaturated compound.

The synthesis of some of the active compounds described above from readily available materials is illustrated by the following reaction schemes:

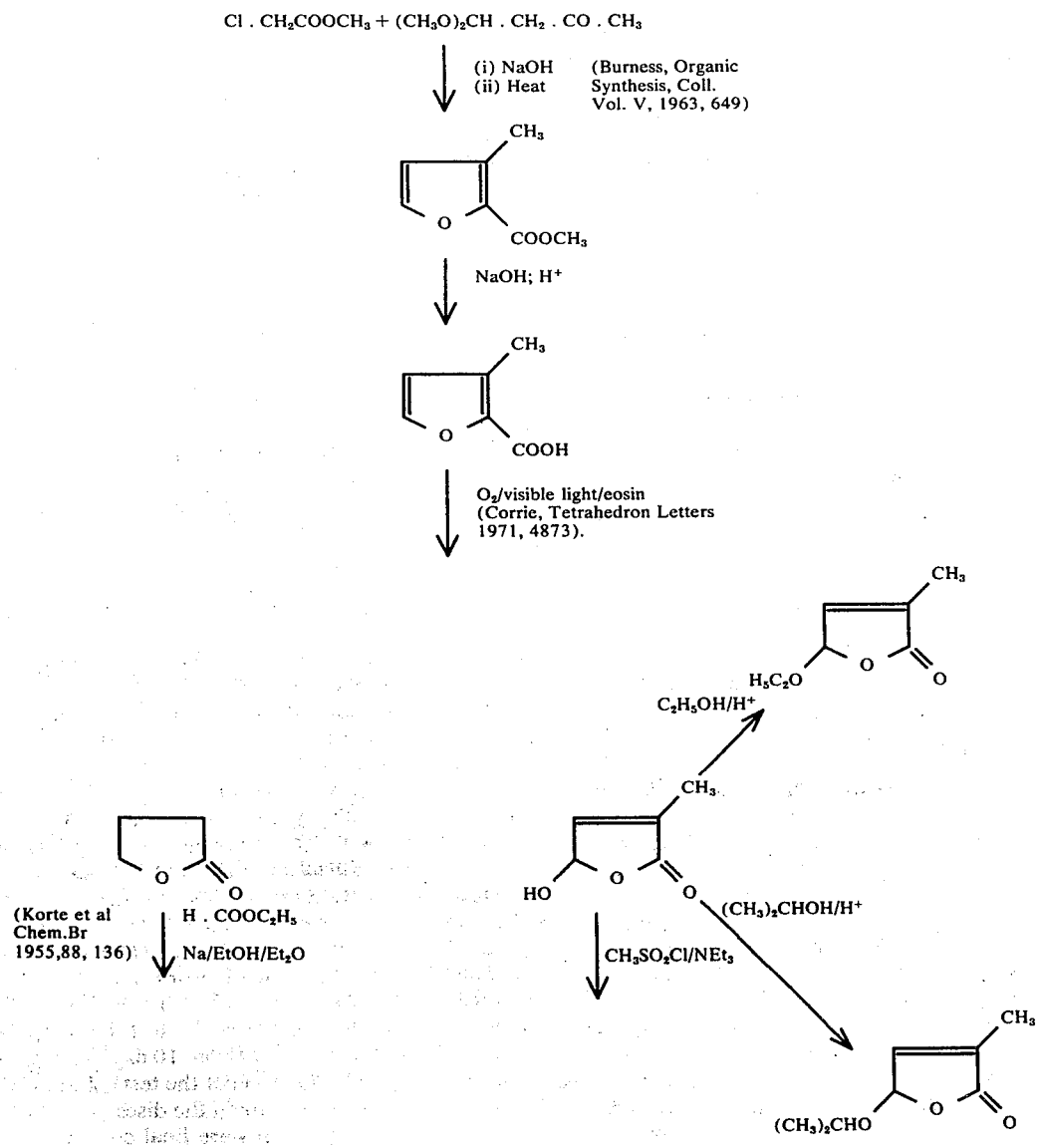

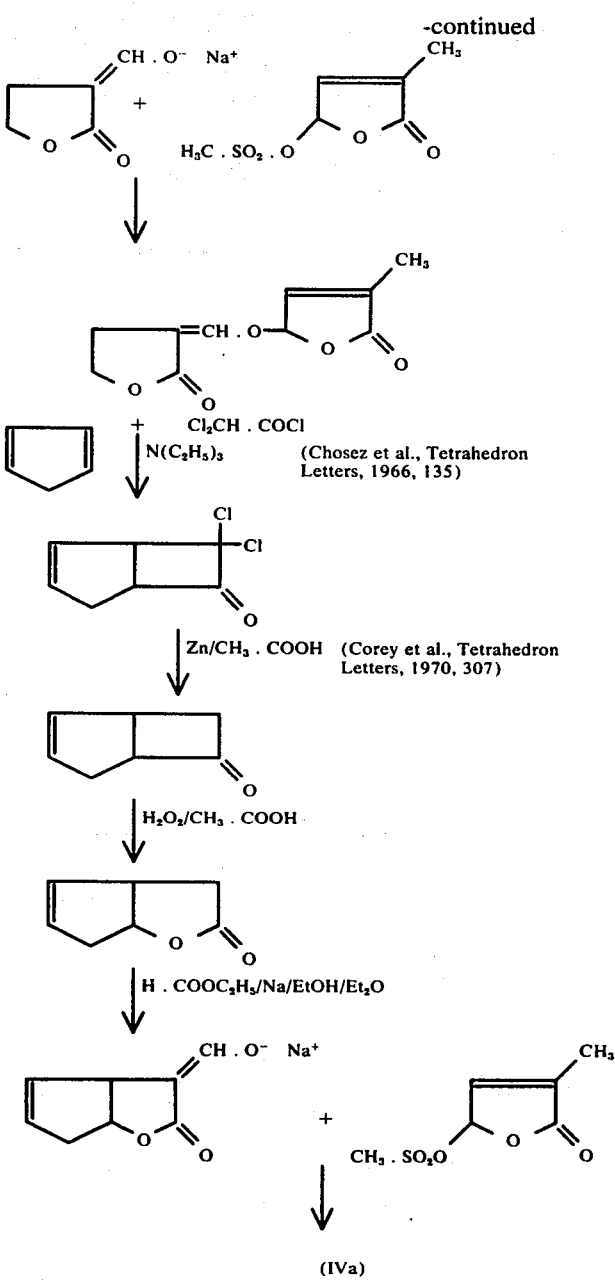

In order to demonstrate the activity of the compounds in promoting the germination of seeds of *Striga hermonthica*, *Striga asiatica*, *Orobanche aegyptiaca*, *Orobanche crenata*, and *Orobanche ramosa*, the following method was used. Seeds of the host plant (sorghum) and of the parasitic weeds were first sterilized with a 1% aqueous sodium hydrochlorite solution for 15 minutes, and then washed with distilled water until free of hypochlorite.

For the purposes of control experiments a natural root exudate of sorghum was prepared by planting sterilized sorghum seeds in pots containing acid-washed silver sand and incubating at 23° C with daily addition of sufficient distilled water to keep moist. After about 1 week the root exudate was extracted by applying suction to the base of the pots.

The Striga or Orobanche seeds were pre-treated by incubating at 23° C under moist conditions, e.g. on moist glass fibre filter paper, for 10-14 days. Usually about 25 seeds on 10 mm discs of the filter paper were employed.

Discs carrying pre-treated seed of Striga or Orobanche were dabbed to remove surplus moisture. Two discs were then placed in each of two replicate dishes, so there were 4 discs per treatment, carrying a total of about 100 seeds. The compounds to be tested were dissolved in ethanol and diluted to the required concentration with distilled water. The amount of ethanol was never greater than 0.5% v/v in the final solution. Freshly prepared solutions were always used. To each disc was added two 16 $\mu$l drops of test solution ("no exudate") or one drop of test solution plus one drop of crude root exudate from 10 day old sorghum plants ("+ exudate"). Dilution of the test solutions by the exudate and/or by moisture in the discs was allowed for so concentrations given were final concentrations. Germination was counted after 2 days at 34° C in the case of Striga and 5 days at 23° C in the case of Orobanche.

TABLE I

Germination tests on *Striga hermonthica*

| Compound | Concentration ppm | % Germination "no exudate" | "+ exudate" |
|---|---|---|---|
| IIIa | 0.001 | 1 | |
| | 0.01 | 27 | |
| | 0.1 | 51 ; 56* | |
| | 1 | 61 | |
| | 10 | 70 | |
| | 50 | — | 70 |
| | 100 | 46 | |
| Control (100% exudate) | | | 72 |
| Control (distilled H₂O) | | 0 | |

*duplicate test carried out subsequently. The substances Ia [R = H; C₂H₅; or CH(CH₃)₂] and II showed little or no activity in promoting the germination of *Striga hermonthica*.

The substances Ia [R=H; C₂H₅; or CH(CH₃)₂] and II showed little or no activity in promoting the germination of *Striga hermonthica*.

TABLE I

Germination tests on *Striga hermonthica*

| Compound | Concentration ppm | % Germination "no exudate" | "+ exudate" |
|---|---|---|---|
| IIIa | 0.001 | 1 | |
| | 0.01 | 27 | |
| | 0.1 | 51 ; 56* | |
| | 1 | 61 | |
| | 10 | 70 | |
| | 50 | — | 70 |
| | 100 | 46 | |
| Control (100% exudate) | | | 72 |
| Control (distilled H₂O) | | 0 | |

*duplicate test carried out subsequently. The substances Ia [R = H; C₂H₅; or CH(CH₃)₂] and II showed little or no activity in promoting the germination of *Striga hermonthica*.

TABLE II

Germination tests on *Orobanche aegyptiaca*

| Compound | Concentration ppm | % Germination "no exudate" | "+ exudate" |
|---|---|---|---|
| | .001 | 0 | |
| | .01 | 12 | |
| | .1 | 19; 27; 44 | |
| | 1 | 59; 60 | |
| Ia(R = H) | 10 | 80; 69 | |
| | 25 | 79 | |
| | 50 | 87 | 75 |
| | 100 | 61; 68 | |
| | 200 | 8 | 30ᵗ |
| | 400 | 0 | |
| Control (100% exudate) | | | 84; 66; 78 |
| Control (distilled H₂O) | | 0; 20; 1 | |

TABLE II-continued

Germination tests on *Orobanche aegyptiaca*

| Compound | Concentration ppm | % Germination "no exudate" | "+ exudate" |
|---|---|---|---|
| | .001 | 0 | |
| | .01 | 0 | |
| | .1 | 19; 2 | |
| Ia(R = C₂H₅) | 1 | 34 | |
| | 10 | 58 | |
| | 25 | 95 | |
| | 50 | 88ᵗ | 61 |
| | 100 | 70; 83ᵗ | |
| Ia(R–C₂H₅) | 200 | 19ᵗ | 0 |
| | 400 | 0 | |
| | .1 | 4 | |
| | 1 | 6 | |
| II | 10 | 24 | |
| | 50 | — | 66 |
| | 100 | 64 | |
| | .001 | 73 | |
| | .01 | 76 | |
| | .1 | 82; 77 | |
| IIIa | 1 | 69ᵗ | |
| | 10 | 71ᵗ | |
| | 50 | — | 61ᵗ |
| | 100 | 47ᵗ | |
| | 0.001 | 0 | |
| | 0.01 | 1 | |
| | 0.1 | 26ᵗ; 11 | |
| Ia[R = CH(CH₃)₂] | 1 | 26ᵗ | |
| | 10 | 48ᵗ | |
| | 50 | | 72 |
| | 100 | 67ᵗ | | t = Evidence of toxicity – some reduction in vigour

As in the case of tests on Striga, replicate tests were carried out on different dates.

It can be seen from Table II that each of the compounds has some activity in promoting the germination of Orobanche, the best being apparently Compound IIIa

TABLE III

Germination tests on *Striga hermonthica*, *Striga asiatica* and *Orobanche aegyptiaca*.

| Compound | Concentration ppm | % Germination S.hermonthica | S.asiatica | O.aegyptiaca |
|---|---|---|---|---|
| IIIa | 0.007 | 3 | 56 | 87 |
| | 0.00007 | 2 | 13 | 87 |
| | 0.0000007 | 0 | 1 | 94 |
| IVa | 0.007 | 22 | 60 | 87 |
| | 0.00007 | 6 | 55 | 89 |
| | 0.0000007 | 0 | 9 | 91 |
| Control Standard exudate | | 65 | 59 | 89 |
| Control Distilled water | | 0 | 2 | 78 |

*In this test the Orobanche seeds have little natural dormancy remaining. It is evident from Table III that compound IVa shows slightly higher activity against *Striga* than compound IIIa.

TABLE IV

Germination tests on *Striga hermonthia*, *Striga asiatica* and *Orobanche ramosa*.

| Compound | | Concentration ppm | % Germination S.hermonthica | S.asiatica | O.ramosa |
|---|---|---|---|---|---|
| IVa | | 1.0 | — | — | 46 |
| | | 0.1 | 58 | 10 | 55 |
| | | 0.01 | 53 | 1 | 51 |
| | | 0.001 | 16 | 0 | — |
| IV | X = single bond | 1.0 | 45 | | 30 |
| | Y = 2H | 0.1 | 44 | | 35 |
| | R' = CH₃ | 0.01 | 21 | | 41 |
| | | 0.001 | 4 | | — |
| IV | X = single bond | 1.0 | 41 | | |

TABLE IV-continued

Germination tests on *Striga hermonthia*, *Striga asiatica* and *Orobanche ramosa*.

| Compound | | Concentration ppm | % Germination | | |
|---|---|---|---|---|---|
| | | | S.hermonthica | S.asiatica | O.ramosa |
| | y = epoxy group | 0.1 | 18 | | |
| | R' = CH₃ | 0.01 | 3 | | |
| | | 0.001 | 0 | | |
| III | X = CH₂ linkage | 1.0 | — | | |
| | R' = CH₃ | 0.1 | 17 | 3* | |
| | | 0.01 | 5 | 5* | |
| | | 0.001 | 0 | 0 | |
| Standard Sorghum exudate | | | 58 | 5 | — |

*anomaly

TABLE V

Germination tests on *Orobanche crenata*

| Compound | Concentration ppm | % Germination |
|---|---|---|
| IIIa | 1.0 | 52.0 |
| | 0.1 | 18.0 |
| | 0.01 | 0.0 |
| | 0.001 | 0.0 |
| IVa | 1.0 | 64.3 |
| | 0.1 | 49.1 |
| | 0.01 | 11.4 |
| | 0.001 | 0.0 |
| Sorghum exudate | | 0.0 |
| Broad bean exudate | | 0.0 |
| Lentil exudate | | 0.0 |
| Distilled water | | 0.0 |

For the following field tests the procedure was as follows:

1. *Striga asiatica* seed was uniformly mixed with black or red soil and the trays were filled on June 18, 1974.
2. Compounds IIIa and IVa were applied at 10, 5 and 1 ppm concentration in both the soils keeping 6 replications for each treatment and one control tray for each soil.
3. Watering was continued everyday up to field capacity.
4. C S H - 1 sorghum seed was planted in both treated and control trays on Aug. 19, 1974.
5. Counting of Striga plants above ground level was taken on Oct. 21, 1974.
6. Counting of Striga plants was also taken after washing the soil between Oct. 31, 1974 and Nov. 8, 1974.

The following results were presented. Values in the brackets indicate the number of plants before washing.

1. Statistical analysis of data indicated that compound IVa recorded the highest significant efficiency (50.00%) over control in controlling Striga.
2. There is no significant difference between concentrations in respect of both the compounds, possibly suggesting that some of the Striga seed was not sensitive to germination at the time the compound was applied.

TABLE VII

| | RED SOIL | | | | | |
|---|---|---|---|---|---|---|
| | COMPOUND IIIa | | | COMPOUND IVa | | |
| Replications | 10 ppm | 5 ppm | 1 ppm | 10 ppm | 5 ppm | 1 ppm |
| 1. | 13 (1) | 15 (2) | 44 (7) | 16 (5) | 22 (6) | 20 (7) |
| 2. | 10 (2) | 32 (4) | 45 (7) | 4 (0) | 11 (3) | 41 (7) |
| 3. | 9 (1) | 38 (6) | 47 (8) | 10 (0) | 31 (6) | 16 (3) |
| 4. | 10 (3) | 44 (3) | 53 (5) | 23 (4) | 26 (5) | 19 (4) |
| 5. | 19 (5) | 21 (2) | 52 (8) | 7 (2) | 8 (3) | 24 (3) |
| 6. | 8 (3) | 18 (3) | 45 (6) | 5 (0) | 12 (2) | 19 (3) |
| Control | — | 48 (6) | | — | 45 (7) | |

Conclusions:

1. Statistical analysis of data indicated that the efficiency between compound IIIa and IVa in controlling Striga is significantly different.
2. Highly significant differences were obtained in between three concentrations in respect of both the compounds.
3. Compound IVa has recorded the highest efficiency (35%) at 10 ppm concentration in controlling Striga.
4. At 1 ppm concentration compound IVa has recorded 15.5% efficiency over control whereas compound IIIa has shown 0.5% efficiency.

TABLE VI

| | BLACK SOIL | | | | | |
|---|---|---|---|---|---|---|
| | COMPOUND IIIa | | | COMPOUND IVa | | |
| Replications | 10 ppm | 5 ppm | 1 ppm | 10 ppm | 5 ppm | 1 ppm |
| 1. | 66 ( 64) | 142 (127) | 158 (140) | 23 ( 18) | 46 ( 22) | 47 ( 40) |
| 2. | 106 (104) | 61 ( 59) | 78 ( 74) | 37 ( 25) | 96 ( 77) | 48 ( 47) |
| 3. | 136 (133) | 87 ( 84) | 125 (112) | 50 ( 35) | 18 ( 13) | 61 ( 43) |
| 4. | 142 (123) | 78 ( 67) | 191 (150) | 30 ( 24) | 8 ( 8) | 33 ( 30) |
| 5. | 222 (167) | 60 ( 58) | 102 (100) | 6 ( 4) | 15 ( 11) | 2 ( 1) |
| 6. | 122 ( 95) | 182 (159) | 103 ( 83) | 7 ( 6) | 16 ( 9) | 36 ( 21) |
| Total | 806 (686) | 610 (554) | 757 (659) | 153 (112) | 199 (140) | 227 (182) |
| Mean | 134 (114) | 102 ( 92) | 126 (110) | 26 ( 19) | 33 ( 23) | 38 ( 30) |
| Control | 126 (115) | | | 90 ( 78) | | |

Conclusions:

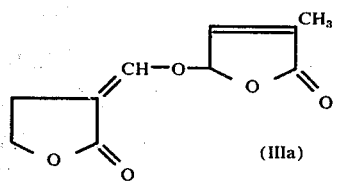

(IIIa)

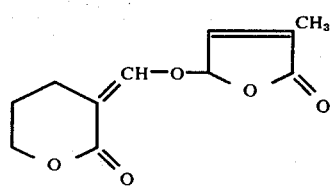

SYNTHESIS OF COMPOUND IIIa i. Preparation of the sodium salt of 3-hydroxymethylene-1,4-butyrolactone — procedure of F. Korte and H. Machleidt, Ber., 88, 136 (1955).

Sodium (11.5g.) was suspended in dry ether (200 ml.) in a 1l. flask equipped with mechanical stirrer. Absolute ethanol (2 ml.) was added and the mixture stirred at room temperture for 3 hrs. A mixture of 1,4-butyrolactone (43g.) and ethyl formate (55.5g., 1.5 equiv.) in ether (100 ml.) was then added over a period of 1 hr. at room temperature. A precipitate was formed immediately and after the addition had been completed no more metallic sodium was present. The mixture was allowed to stand at −20° C overnight. It was filtered under vacuum and washed quickly with dry ether, then transferred while still wet with ether to a vacuum oven. The salt was dried at 40° C in vacuo. Yield, 64.5g. (95%).

ii. Preparation of Compound IIIa

The mesylate of compound Ia (19.04g.) was dissolved in 1,2-dimethoxyethane (200 ml.) and the sodium salt of 3-hydroxymethylene-1,4-butyrolactone (15g.) was added and this mixture stirred at room temperature for 24 hrs. The mixture was then filtered and the residue washed well with 1,2-dimethoxyethane. The filtrate was evaporated to dryness and the residue taken up in methylene chloride (20 ml.). Ether (60 ml.) was added carefully and the product allowed to crystallize. The white crystalline product was removed by filtration and washed with ether. Yield 12g. (60%), mp 92°–94° C. (Found: C, 57.04; H, 4.7 $C_{10}H_{10}O_5$ requires C, 57.14; H, 4.76%).

SYNTHESIS OF COMPOUND III (R' = CH₃, X = —CH₂—)

i. Preparation of the Sodium salt of δ-Valerolactone

Sodium metal (2.30g.) was suspended in dry ether (150 ml.) in a 500 ml. 3 neck round-bottom flask equipped with stirrer, heating mantle, dropping funnel and reflux condenser. Ethanol (1.5 ml.) was then added and the mixture stirred at room temperature for 3 hrs. The mixture was then heated to reflux and a mixture of δ-valerolactone (10g.) and ethyl formate (22.2g., 3 equivalents) in ether (50 ml.) added over a period of 1.5 hrs. The mixture was then stirred under reflux for 15 hrs., cooled and the sodium salt removed by vacuum filtration. It was washed well with dry ether and then dried in vacuo at 40° C. Yield 13g. (85.5%).

ii. Preparation of Compound III (R' = CH₃, X = —CH₂—)

The mesylate of compound Ia (1.26g.) was dissolved in 1,2-dimethoxyethane (20 ml.). The sodium salt of 3-hydroxymethylene-δ-valerolactone (1.5g., 1.5 equiv.) was added and the mixture stirred at room temperature for 4 hours. The mixture was then poured into icewater (100 ml.) and extracted with methylene chloride (2 × 100 ml.). The organic extracts were washed with water (2 × 50 ml.), combined, dried over magnesium sulphate, and evaporated to dryness. The semi-crystalline residue was taken up in methylene chloride (1.5 ml.), and ether (6 ml.) carefully added. The product crystallized and was removed by filtration and washed well with cold ether.

Yield 1.05g. (71%), mp 105°–107° C.

SYNTHESIS OF COMPOUND IVa

Reaction (i)

↓ Et₃N

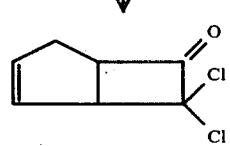

Reaction (ii)

↓ Zn/HOAc

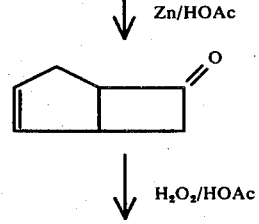

Reaction (iii)

↓ H₂O₂/HOAc

SYNTHESIS OF COMPOUND IVa-continued

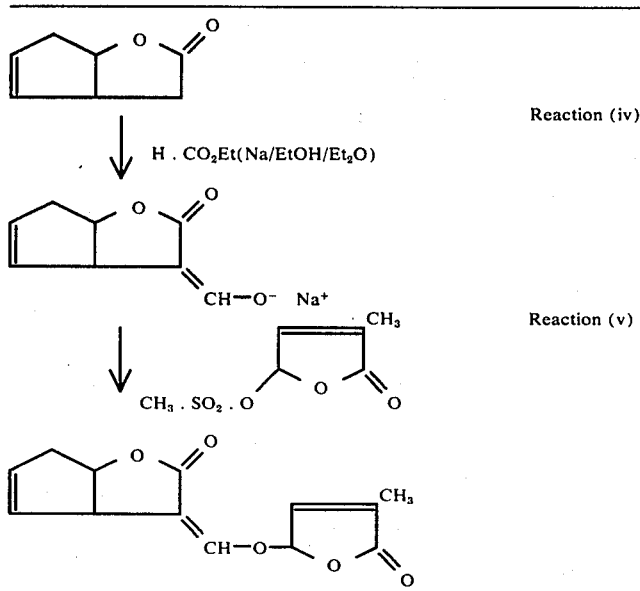

Reaction (iv)

Reaction (v)

Reaction 1

To a 3 l. 3-neck flask equipped with mechanical stirrer and heating mantle, was added a solution of freshly prepared cyclopentadiene (156g.) and dichloroacetyl-chloride (117g.) in n-pentane (2000 ml.). The mixture was brought to reflux and triethylamine (86g.) in n-pentane (500 ml.) was added over a period of 0.5 hrs. The resulting heavy slurry was refluxed for a further 0.5 hrs. then filtered and the residue washed well with n-pentane. The filtrate was reduced in vacuo to 800 ml., transferred to a separating funnel and washed twice with water (2 × 200 ml.). The organic layer was dried over magnesium sulphate, the solvent removed in vacuo and the residue vacuum distilled, bp 72°–73° C at 3.5mm. Yield 108g. (77%).

Reaction 2

To a 2 l. 3-neck flask equipped with a mechanical stirrer was added a solution of the dichloroketone product of reaction 1 (100g.) in 90% acetic acid (aqueous) (900 ml.). Zinc dust (91g., 2.5 equiv.) was added portionwise to the cooled stirred solution over a period of 1 hr., the temperature beinng maintained below 40° C during this period. The cooling bath was replaced with a heating mantle and the mixture heated over 1 hr. to 100° C and maintained at that temperature. After 2 hrs. a further amount of zinc (91g., 2.5 equiv.) was added and the mixture stirred at 100° C for a further 1 hr. The mixture was then cooled to <10° C and filtered. The filtrate was poured into icewater (2000 ml.) and transferred to a separating funnel and extracted 3 times with methylene chloride (3 × 1000 ml.). The extracts were washed with water (4 × 1000 ml.), then with saturated sodium bicarbonate solution (1000 ml.). The combined extracts were dried with magnesium sulphate, the solvent removed in vacuo, and the residue vacuum distilled bp 61°–62° C at 14mm. Yield 51.4g. (86%).

Reaction 3

The ketone product of reaction 2 (40g.) was dissolved in acetic acid/$H_2O$ (7/1; 400 ml.). Hydrogen peroxide (30%) (94.6 ml., 2.5 equiv.) was added when the mixture had been cooled to 0° C. The mixture was then stored at 0° C for 18 hrs. then diluted with icewater (400 ml.) and extracted twice with methylene chloride (2 × 200 ml.). The organic extracts were washed with water (3 × 200 ml.) and with saturated sodium bicarbonate solution (200 ml.). The combined extracts were dried with magnesium sulphate, the solvent removed in vacuo and the residue vacuum distilled, bp 66°–67° at 0.3 mm. Yield 41.4g. (90%).

Reaction 4

A 250 ml. 3 neck flask equipped with magnetic stirrer, dropping funnel and nitrogen inlet was charged with dry diethyl ether (100 ml.). Sodium (2.83g.) and ethanol (1 ml.) was added to this mixture and stirred at room temperature for 3 hrs. The dropping funnel was then charged with a mixture of the lactone product of reaction 3 (15g.) and ethyl formate (10.2g.) in ether (50 ml.). This mixture was added dropwise to the sodium/sodium ethoxide slurry over a period of 1 hr. at room temperature. The mixture was then stirred for a further 1 hr. and then cooled to −20° C for 16 hrs. The sodium salt was removed by vacuum filtration and washed quickly with dry ether. The hygroscopic sodium salt, still very wet with ether, was rapidly transferred to a vacuum oven and dried at 40° C in vacuo. Yield 19.3g. (90%).

Reaction 5

The mesylate (19.4g.; see below) was dissolved in 1,2 dimethoxyethane (200 ml.) and cooled to 0° C. The sodium salt product from reaction 4 (18.5g.; 1.1 equiv.) was added and the mixture stirred at 0° C for 3 hrs. The precipitated sodium mesylate was removed by filtration and washed well with dimethoxyethane. The filtrate was evaporated to dryness at <40° C and the residue taken up in methylene chloride (200 ml.). The solution was washed with water (2 × 100 ml.), dried with magnesium sulphate and evaporated to dryness. Crude yield 24.6g. (98%). After crystallization from methylene chloride/ether the yield was 16.2g. (65%) mp 128–130° C. Analysis: $C_{13}H_{12}O_5$ requires C, 62.90; H, 4.84. Found: C, 62.96; H, 4.68%.

Preparation of Mesylate.

A 2 l. 3 neck flask equipped with cooling bath and mechanical stirrer was charged with the pseudo acid (compound Ia; R = H) (80g.), mesyl chloride (81.15g., 1:01 equiv.) and methylene chloride (800 ml.). This mixture was cooled to 0° C and triethylamine (74.4g.; 102.4 ml., 1.05 equiv.) in methylene chloride (300 ml.) was added over a period of 4½ hrs. The mixture was then stirred at 0° C for 8 hrs., and then poured into water (500 ml.) in a separating funnel. The organic layer was washed once more with water (250 ml.), dried over magnesium sulphate, and the solvent removed in vacuo. The residue was taken up in warm ether (100 ml.) and allowed to crystallize first at room temperture and then at —20° C. The product was removed by vacuum filtration and washed sparingly with ether. Yield 92g. (70%).

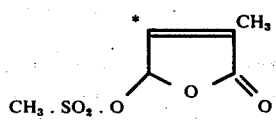

What we claim as our invention is:

1. A method for the control of at least one of the parasitic weeds, Striga hermonthica, S. asiatica (lutea); Orobanche crenata, O. ramosa and O. aegyptiaca, which comprises contacting dormant seeds thereof, in the absence of an actively growing host plant, with a compound corresponding to the formula:

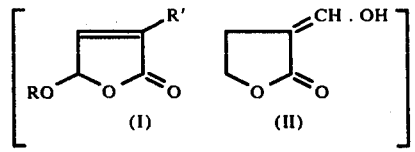

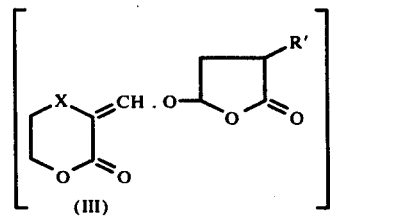

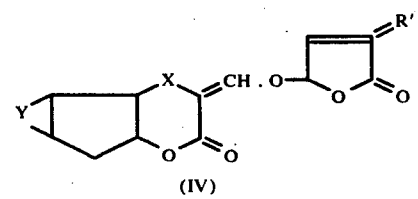

wherein R' is H or $C_1$ to $C_5$ alkyl, X represents a single bond or a —$CH_2$— linkage, and Y represents two hydrogen atoms, and additional bond or an epoxy group.

2. A method according to claim 1 wherein the compound is a compound of formula (IV) wherein R' is methyl, X is a single bond and Y is an additional bond.

3. A method according to claim 1 wherein the parasitic weed is Striga hermonthica or S. asiatica (lutea).

4. A method according to claim 1 wherein the parasitic weed is Orbanche aegyptiaca.

5. A method according to claim 1 wherein the parasitic weed is Orobanche crenata.

6. A method according to claim 1 wherein the parasitic weed is Orobanche ramosa.

7. A method according to claim 1 for the control of the parasitic weed Striga hermonthica which comprises contacting the dormant seeds thereof, in the absence of an actively growing host plant, with a compound of formula (IV) wherein R' is methyl, X is a single bond and Y is an additional bond.

8. A method according to claim 1 for the control of the parasitic weed Striga asiatica (lutea) which comprises contacting the dormant seeds thereof, in the absence of an actively growing host plant, with a compound of formula (IV) wherein R' is methyl, X is a single bond and Y is an additional bond.

9. A method according to claim 1 for the control of the parasitic weed Orobanche aegyptiaca which comprises contacting the dormant seeds thereof, in the absence of an actively growing host plant, with a compound of formula (IV) wherein R' is $CH_3$, X is a single bond and Y is an additional bond.

10. A method according to claim 1 for the control of the parasitic weed Orobanche crenata which comprises contacting the dormant seeds thereof, in the absence of an actively growing host plant, with a compound of formula (IV) wherein R' is $CH_3$, X is a single bond and Y is an additional bond.

11. A compound corresponding to the formula

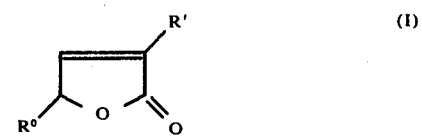

wherein R is $C_3$ to $C_8$ alkyl and R' is H or $C_1$ to $C_5$ alkyl;

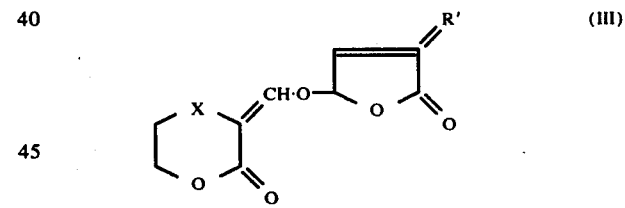

—$CH_2$— linkage and R' is H or $C_1$ to $C_5$ alkyl; or

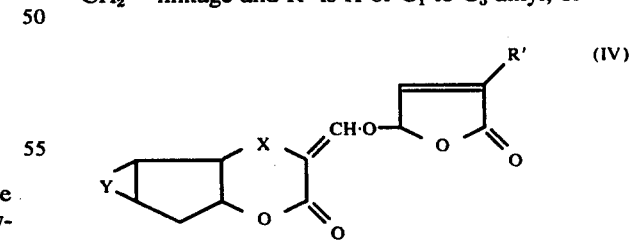

wherein R' is $C_1$ to $C_5$ alkyl, X is single bond and Y is an additional bond or an epoxy group, or wherein R' is $C_1$ to $C_5$ alkyl, X is a —$CH_2$— linkage and Y is two hydrogen atoms, a single bond or an epoxy group.

12. A compound according to claim 11 wherein the compound corresponds to the formula: (V) wherein R' is methyl, X is a single bond and Y is an additional bond.

13. A process for the preparation of a compound of formula (IV) as defined in claim 1 which comprises coupling a compound of the formula

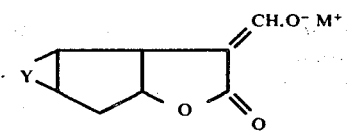

wherein Y is two hydrogen atoms, an additional bond or an epoxy group, and M+ is the ion of an alkali metal, with a compound of the formula

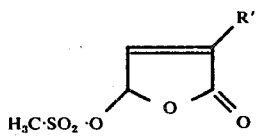

wherein R' is H or $C_1$ to $C_5$ alkyl.

14. A process as claimed in claim 13 wherein in the starting materials X is a single bond Y is an additional bond and R' is $CH_3$.

15. A process as claimed in claim 13 wherein in the starting materials M+ is the sodium ion.

16. A herbicidal composition suitable for combatting at least one of the parasitic weeds *Striga hermonthica, S. asiatica, Orobanche crenata, O. ramosa* and *O. aegyptiaca*, which comprises a compound of formula (IV) as defined in claim 1 in association with a suitable inert carrier or diluent.

17. A herbicidal composition suitable for combatting at least one of the parasitic weeds *Striga hermonthica S. asiatica* and *Orobanche aegyptiaca*, which comprises a compound of formula (IV) defined in claim 1 wherein R' is methyl, X is a single bond, and Y is an additional bond in association with a suitable inert carrier or diluent.

18. A composition as defined in claim 17 wherein the carrier or diluent is a solid carrier or diluent or a liquid carrier or diluent containing a surface active agent.

* * * * *

UNITED STATES PATENT AND TRADEMARK OFFICE
CERTIFICATE OF CORRECTION

PATENT NO. : 4,002,459
DATED : January 11, 1977
INVENTOR(S) : Alan W. Johnson et al.

It is certified that error appears in the above-identified patent and that said Letters Patent are hereby corrected as shown below:

Claim 1, delete formulae (I), (II) and (III) and the brackets about these formulae Claim 1, change formula (IV) to read as follows:

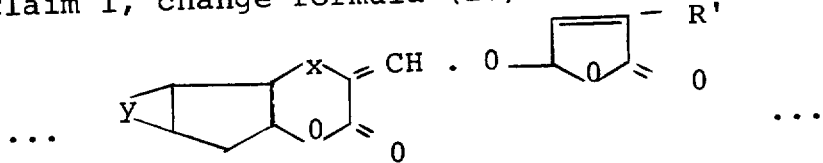

Claim 1, last line, change "and" to ...an...

Claim 11, delete formulae (I) and (III) and each of the attendant lines following each formula Claim 11, first line after the formula (IV) after "X is" insert ...a...

Claim 11, last line, change "a single bond" to ...an additional bond...

Claim 12, line 2, change "(V)" to ...(IV)...

UNITED STATES PATENT OFFICE
CERTIFICATE OF CORRECTION

Patent No. 4,002,459  Dated January 11, 1977

Inventor(s) Alan W. Johnson et al.  Page 2 of 2

It is certified that error appears in the above-identified patent and that said Letters Patent are hereby corrected as shown below:

Claim 13, change the formula to read as follows:

... 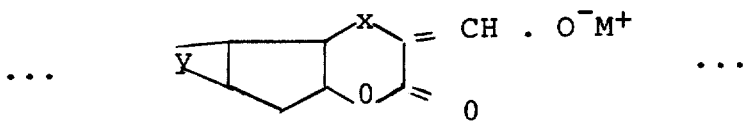 ...

Claim 13, second line after the first structural formula, after "group," insert ...X represents a single bond or a -$CH_2$- linkage...

Signed and Sealed this

Tenth Day of May 1977

[SEAL]

Attest:

RUTH C. MASON
Attesting Officer

C. MARSHALL DANN
Commissioner of Patents and Trademarks